(12) United States Patent
Inoue et al.

(10) Patent No.: US 11,554,116 B2
(45) Date of Patent: Jan. 17, 2023

(54) AGENT FOR PREVENTING AND/OR TREATING ALZHEIMER'S DISEASE

(71) Applicant: KYOTO UNIVERSITY, Kyoto (JP)

(72) Inventors: Haruhisa Inoue, Kyoto (JP); Takayuki Kondo, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 90 days.

(21) Appl. No.: 16/626,686

(22) PCT Filed: Jun. 27, 2018

(86) PCT No.: PCT/JP2018/024465
§ 371 (c)(1),
(2) Date: Dec. 26, 2019

(87) PCT Pub. No.: WO2019/004321
PCT Pub. Date: Jan. 3, 2019

(65) Prior Publication Data
US 2020/0222386 A1    Jul. 16, 2020

(30) Foreign Application Priority Data
Jun. 28, 2017    (JP) .............................. JP2017-126808

(51) Int. Cl.
*A61K 31/48*    (2006.01)
*A61P 25/28*    (2006.01)

(52) U.S. Cl.
CPC .............. *A61K 31/48* (2013.01); *A61P 25/28* (2018.01)

(58) Field of Classification Search
CPC ........... A61K 3/48; A61K 31/48; A61P 25/28
See application file for complete search history.

(56) References Cited

U.S. PATENT DOCUMENTS 6,060,483 A    5/2000    Mantegani et al.
2004/0058873 A1    3/2004    Esmond et al.
(Continued)

FOREIGN PATENT DOCUMENTS

JP    2000-513365 A    10/2000
JP    2001-514663 A    9/2001
(Continued)

OTHER PUBLICATIONS

Web printout of https://www.nia.nih.gov/health/alzheimers-disease-fact-sheet, content reviewed May 22, 2019, pp. 1-8. (Year: 2019).*
(Continued)

*Primary Examiner* — Craig D Ricci
*Assistant Examiner* — Janet L Coppins
(74) *Attorney, Agent, or Firm* — Oblon, McClelland, Maier & Neustadt, L.L.P.

(57) ABSTRACT

The present invention provides a prophylactic and/or therapeutic agent for Alzheimer's disease containing a compound
(Continued)

represented by the formula (I) or the formula (II) or a salt thereof. Each symbol in the formulas (I) and (II) are as described in the attached DESCRIPTION:

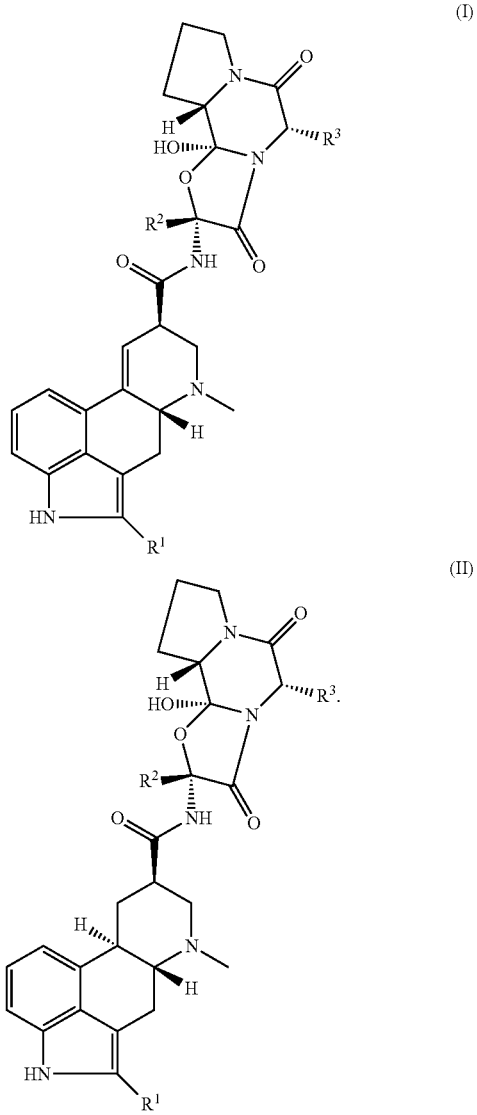

2 Claims, 2 Drawing Sheets (56) References Cited

U.S. PATENT DOCUMENTS

| 2004/0060077 | A1 | 3/2004 | Esmond et al. |
|---|---|---|---|
| 2005/0043242 | A1 | 2/2005 | Esmond et al. |
| 2009/0280192 | A1 | 11/2009 | Esmond et al. |
| 2014/0038927 | A1 | 2/2014 | Cohen et al. |
| 2019/0008860 | A1 | 1/2019 | Inoue et al. |

FOREIGN PATENT DOCUMENTS

| WO | WO 98/39967 A1 | 9/1998 |
|---|---|---|
| WO | WO 2012/117073 A2 | 9/2012 |
| WO | WO 2017/115873 A1 | 7/2017 |

OTHER PUBLICATIONS

Lei, X. L. et al., "The FDA-approved natural product dihydroergocristine reduces the production of the Alzheimer's disease amyloid-G peptides", Scientific Reports, vol. 5, Nov. 16, 2015, pp. 1-11. (Year: 2015).*
Borchelt et al, Neuron, vol. 17, 1005-1013, Nov. 1996. (Year: 1996).*
Wiltfeng et al, Journal of Neurochemistry, 2007, 101, 1053-1059 (Year: 2007).*
Ono et al, J Neuroscience Research (2013), vol. 91, pp. 1371-1381. (Year: 2013).*
International Search Report dated Sep. 11, 2018, in PCT/JP2018/024465, 2 pages.
English translation of the International Preliminary Report on Patentability and Written Opinion dated Dec. 21, 2019, in PCT/JP2018/024465, 9 pages.
Lei, X. L. et al., "The FDA-approved natural product dihydroergocristine reduces the production of the Alzheimer's disease amyloid-β peptides", Scientific Reports, vol. 5, Nov. 16, 2015, 11 pages.
Milvio, C., "Dihydroergocristine in the treatment of organic brain syndrome. Dose-finding-study against placebo", Arzneimittel Forschung (Drug Research), vol. 42, No. II, Nov. 1992, pp. 1399-1402.
Ono, K. et al., "Anti-Parkinsonian agents have anti-amyloidogenic activity for Alzheimer's β-amyloid fibrils in vitro", Neurochemistry International, Mar. 2006, vol. 48, No. 4, pp. 275-285.
Cucinotta, D. et al., "Dihydroergocryptine vs. placebo in dementia of Alzheimer type: interim results of a randomized multicenter study after a 1-year follow-up", Archives of Gerontology and Geriatrics, 1996, vol. 22, pp. 169-180.
Tanzi, R. E., "The Genetics of Alzheimer Disease", Cold Spring Harbor Perspectives in Medicine, Jul. 25, 2012, pp. 1-10.
Corbett, A. et al., "Drug repositioning in Alzheimer's disease", Frontiers in Bioscience, Scholar, vol. 7, Jun. 1, 2015, pp. 184-188.
Yahata, N. et al., "Anti-Ab Drug Screening Platform Using Human iPS Cell-Derived Neurons for the Treatment of Alzheimer's Disease", Plos One, e25788, vol. 6, Issue 9, Sep. 2011, 11 pages.
Liu, Q. et al., "Effect of Potent γ-Secretase Modulator in Human Neurons Derived From Multiple Presenilin 1-Induced Pluripotent Stem Cell Mutant Carriers", JAMA Neurol., vol. 71, Dec. 2014, pp. 1481-1489.
Mertens, J. et al., "APP Processing in Human Pluripotent Stem Cell-Derived Neurons Is Resistant to NSAID-Based g-Secretase Modulation", Stem Cell Reports, vol. 1, Dec. 17, 2013, pp. 491-498.
Extended European Search Report dated Feb. 15, 2021 in European Patent Application No. 18825243.1, 11 pages.
Sudha S. Savant et al., "The Role of Inflammation and Inflammatory Mediators in the Development, Progression, Metastasis, and Chemoresistance of Epithelial Ovarian Cancer" Cancers, vol. 10, No. 8, XP055772089, 2018, pp. 1-30.
J. Sevigny, et al., The antibody aducanumab reduces Aβ plaques in Alzheimer's disease, Nature, Sep. 1, 2016; 537(7618):50-56.
J. Maloney, et al., Molecular Mechanism of Alzheimer Disease Protection by the A673T Allele of Amyloid Precursor Protein, J Biol Chem. Nov. 7, 2014; 289(45):30990-1000.
P. Phuapradit, et al., British Medical Journal, Apr. 22, 1978, 1052-1053.
T. Jonssonk, et al., A mutation in APP protects against Alzheimer's disease and age-related cognitive decline, Nature, Aug. 2, 20212, 488, 96-99.
Office Action dated Aug. 26, 2022, in Chinese patent application 201880043522.6, with English translation—25 pages.
Imamura T, "Bromocriptine treatment for perseveration in demented patients." *Alzheimer Dis Assoc Disord*. Jun. 1998;12(2):109-13.

* cited by examiner

AGENT FOR PREVENTING AND/OR TREATING ALZHEIMER'S DISEASE

CROSS-REFERENCE TO RELATED APPLICATIONS

The present application is a 35 U.S.C. § 371 national stage patent application of International patent application PCT/JP2018/024465, filed on Jun. 27, 2018, which is based on and claims the benefits of priority to Japanese Application No. 2017-126808, filed on Jun. 28, 2017. The entire contents of these applications are incorporated herein by reference.

TECHNICAL FIELD

The present invention relates to a prophylactic and/or therapeutic agent for Alzheimer's disease. More particularly, the present invention relates to a prophylactic and/or therapeutic agent for Alzheimer's disease, which contains a peptide-type ergot alkaloid.

BACKGROUND ART

Alzheimer's disease (AD) is a type of dementia with main symptoms of decline in cognitive function and change of personality. AD brain lesions are characterized by degeneration and disappearance of nerve cells and cerebral atrophy associated therewith, frequent occurrence of senile plaques, and frequent occurrence of neurofibrillary tangles (NFT). Of these, senile plaques are known to be aggregation and accumulation of amyloid β (Aβ) peptide. Aβ is a peptide consisting of 38-43 amino acids produced as a result of cleavage of amyloid precursor protein (APP) by β- and γ-secretases. Of these, Aβ42 is known to have high aggregation activity and toxicity against nerve cells, and it has been reported that an increase in Aβ 42/40 ratio is observed in cells having causative mutation for familial Alzheimer's disease (FAD).

Conventionally, it is widely recognized that decreasing the amount of Aβ, particularly the amount of Aβ42, becomes a key point for suppressing the onset of AD. This is clear also from the fact that some of the modulator drugs of β- or γ-secretase have been shown to reduce the onset of AD in a mouse model overexpressing presenilin 1 (PSEN1) or mutant APP.

Despite significant success in preclinical tests using AD model mice, these modulator drugs failed in many clinical tests when used for human.

From the results of antibody therapy, it has heretofore been shown that lesions caused by accumulation of Aβ, including senile plaques, are reversible. Unfortunately, however, clinical effectiveness has not been obtained even when Aβ accumulation was eliminated, and intervention at a stage before developing mild cognitive impairment (MCI) is considered to be necessary. Amyloid PET (positron emission tomography) has also demonstrated that the pathological change of Aβ already precedes in the stage before developing MCI, and intervention in the pre-symptomatic stage is necessary for people at risk of AD and predicted to be present in a large number. In particular, the importance of preventive therapy including dominantly inherited Alzheimer network (DIAN) research is emphasized. However, aggressive application of very expensive antibody medicines to such subjects is not realistic. In addition, treatments by oral administration of many compounds targeting Aβ have also been tried, but none of them have been placed on the market due to the problems of side effects. Therefore, solutions of drug safety and pre-emptive treatment (early treatment) are considered important for making drugs targeting Aβ effective.

On the other hand, a rapid increase in AD patients associated with the advancement of aging society is putting pressure on the medical economy. As of 2010, the medical expenses for 35 million AD patients are $604 billion per year. AD patients are expected to increase to 114 million in 2050 and the medical expenses are predicted to rise further. Under these circumstances, importance is placed on drug repositioning for AD treatment, that is, diverted application of existing drugs (non-patent document 1). Enormous clinical information relating to safety and pharmacokinetics of existing drugs has already been accumulated (Chembl database and the like) and the safety has already been established. Thus, intervention as a pre-emptive treatment for people at risk of AD who do not have clinical symptoms but have been judged positive by amyloid test can be expected. In fact, Valsartan (depressor) and Liraglutide (antidiabetic drug) have proceeded to clinical trial. As described above, the importance of drug repositioning in the AD treatment is predicted to further increase in the future.

Incidentally, a cell causing the disease that was induced to differentiate from patient-derived iPS cells (disease iPS cells) is assumed to reproduce pathology of the patient in vitro. Therefore, it is expected as a promising system for efficacy evaluation. In recent reports relating to nerve cells derived from human iPS cells, the importance of human nerve cell as a tool for evaluating drug responsiveness is stressed (non-patent documents 2-4).

DOCUMENT LIST

Non-Patent Documents non-patent document 1: Front. Biosci. (Schol. Ed). 7, 184-8 (2015)
non-patent document 2: PLoS One 6, e25788 (2011)
non-patent document 3: JAMA Neurol. 71, 1481-9 (2014)
non-patent document 4: Stem Cell Reports 1, 491-498 (2013)

SUMMARY OF THE INVENTION

Problems to be Solved by the Invention

An object of the present invention is to provide a novel and effective prophylactic and/or therapeutic approach and the like to Alzheimer's disease.

Means of Solving the Problems

In an attempt to achieve the above-mentioned object, the present inventors first induced differentiation into cerebral cortex nerve cell from an induced pluripotent stem cell (iPS cell) established from familial AD patient. Using the nerve cell, they constructed an experimental system for monitoring metabolic dynamics of amyloid β protein (amyloid beta: Aβ) as a pathogenic substance of AD. Using the experimental system, screening analysis of an existing drug library was performed and a medicament that decreases Aβ production was searched for. As a result of the search, it was found that addition of bromocriptine (bromocriptine mesylate) decreases production of Aβ, and an analogous compound of bromocriptine also decreases production of Aβ. The present inventors have conducted further studies based on these findings and completed the present invention.

That is, the present invention provides the following.

[1] A prophylactic and/or therapeutic agent for Alzheimer's disease comprising a compound represented by the formula (I):

or the formula (II):

[in the formulas (I) and (II),
R$^1$ is a hydrogen atom or a halogen atom; and
R$^2$ and R$^3$ are each independently a straight chain or branched alkyl group having 1-5 carbon atoms or an aryl group having 6-10 carbon atoms]
or a salt thereof.

[2] The agent of [1] wherein the R$^1$ is a bromine atom.
[3] The agent of [1] or [2] wherein the R$^2$ is a methyl group or an isopropyl group, and the R$^3$ is an isopropyl group, an isobutyl group, a sec-butyl group or a benzyl group.
[4] The agent of [1] wherein the aforementioned compound is at least one kind of compound selected from the group consisting of α-ergocryptine, bromocriptine, ergocristine, dihydroergocristine, ergotamine and dihydroergotamine, or a salt thereof.

[5] The agent of [4] wherein the aforementioned compound is bromocriptine or a salt thereof.

[6] The agent of any of [1]-[5] wherein the aforementioned Alzheimer's disease is caused by mutation of presenilin 1.

[7] A method for preventing and/or treating Alzheimer's disease in a mammal comprising administering an effective amount of a compound represented by the formula (I):

or the formula (II):

[in the formulas (I) and (II),
R$^1$ is a hydrogen atom or a halogen atom; and
R$^2$ and R$^3$ are each independently a straight chain or branched alkyl group having 1-5 carbon atoms or an aryl group having 6-10 carbon atoms]
or a salt thereof to the mammal.

[8] A compound represented by the formula (I):

(I)

or the formula (II):

(II)

[in the formulas (I) and (II),
$R^1$ is a hydrogen atom or a halogen atom; and
$R^2$ and $R^3$ are each independently a straight chain or branched alkyl group having 1-5 carbon atoms or an aryl group having 6-10 carbon atoms]
or a salt thereof, for use in the prophylaxis and/or treatment of Alzheimer's disease.

Effect of the Invention

According to the present invention, it becomes possible to prevent and/or treat Alzheimer's disease for which an effective prophylactic or therapeutic drug has never existed before. Particularly, when existing drugs confirmed to be safe are used as active ingredients, the fear of side effects is less.

DESCRIPTION OF EMBODIMENTS

The present invention is explained in the following. The terms used in the present specification have the meanings generally used in the pertinent field unless otherwise specified.

The present invention provides a prophylactic and/or therapeutic agent for Alzheimer's disease containing peptide-type ergot alkaloid (hereinafter to be also referred to as "the medicament of the present invention")

In the present invention, the "peptide-type ergot alkaloid" (hereinafter sometimes to be abbreviated as "the compound of the present invention") is also called ergopeptine and is a derivatives in which three peptides and the like are added at the same position as the amide group of the lysergic acid derivative in the ergoline ring. This structure contains proline and two other α amino acids, which are linked by cyclol. The structural formula of the peptide-type ergot alkaloid used in the present invention is shown as the following formula (I) or (II).

in the above-mentioned formulas (I) and (II), $R^1$ is a hydrogen atom or a halogen atom; and
$R^2$ and $R^3$ are each independently a straight chain or branched alkyl group having 1-5 carbon atoms or an aryl group having 6-10 carbon atoms.

Examples of the halogen atom include fluorine atom, chlorine atom, bromine atom and iodine atom. As shown in the below-mentioned Examples, from the aspect of reduction of the Aβ42/40 ratio, modification with the bromo group at the 2-position in the ergoline ring structure of the compound of the present invention is preferable. Therefore, the halogen atom is preferably a bromine atom. Examples of the alkyl group include groups such as methyl, ethyl, n-propyl, isopropyl, n-butyl, isobutyl, sec-butyl, tert-butyl, n-pentyl, isopentyl, tert-pentyl, neopentyl, 2-pentyl, 3-pentyl and the like. Preferred $R^2$ is methyl group or isopropyl group, and preferred $R^3$ is isopropyl group, isobutyl group or sec-butyl group. Examples of the aryl group include phenyl group, benzyl group, tolyl group, o-xylyl group, naphthyl group and the like and preferred is benzyl group.

As described in the below-mentioned Examples, it was shown that the structure of the peptide-type ergot alkaloid represented by the formula (I) or formula (II) is important for reducing the production amount of Aβ. Therefore, while the peptide-type ergot alkaloid that can be used in the present invention is not particularly limited as long as it is represented by the formula (I) or the formula (II), specific examples include ergotoxins in which amino acid at position $R^2$ is valine and ergotamines in which amino acid at position $R^2$ is alanine. Examples of the ergotoxins include ergocristine, dihydroergocristine, ergocornine, dihydroergocornine, α-ergocryptine (and bromocriptine which is a compound wherein hydrogen atom for $R^1$ of the compound is substituted by bromine atom), dihydroα-ergocryptine, β-ergocryptine, dihydro-β-ergocryptine, shown in Table 1, and the like. Examples of the ergotamines include ergotamine, dihydroergotamine, ergovaline, dihydroergovaline, α-ergosine, dihydroα-ergosine, β-ergosine, dihydroβ-ergosine and the like. Among these, α-ergocryptine, bromocriptine, ergocristine, dihydroergocristine, ergotamine and dihydroergotamine are preferred.

TABLE 1

| compound name | $R^1$ | $R^2$ | $R^2$-position amino acid | $R^3$ | $R^3$-position amino acid | structural formula |
|---|---|---|---|---|---|---|
| ergocristine | H | $CH(CH_3)_2$ | valine | benzyl | phenylalanine | formula (I) |
| dihydroergocristine | H | $CH(CH_3)_2$ | valine | benzyl | phenylalanine | formula (II) |
| ergocornine | H | $CH(CH_3)_2$ | valine | $CH(CH_3)_2$ | valine | formula (I) |
| dihydroergocornine | H | $CH(CH_3)_2$ | valine | $CH(CH_3)_2$ | valine | formula (II) |
| α-ergocryptine | H | $CH(CH_3)_2$ | valine | $CH_2CH(CH_3)_2$ | leucine | formula (I) |
| dihydro-α-ergocryptine | H | $CH(CH_3)_2$ | valine | $CH_2CH(CH_3)_2$ | leucine | formula (II) |
| β-ergocryptine | H | $CH(CH_3)_2$ | valine | $CH(CH_3)CH_2CH_3$ (S) | isoleucine | formula (I) |
| dihydro-β-ergocryptine | H | $CH(CH_3)_2$ | valine | $CH(CH_3)CH_2CH_3$ (S) | isoleucine | formula (II) |
| ergotamine | H | $CH_3$ | alanine | benzyl | phenylalanine | formula (I) |
| dihydroergotamine | H | $CH_3$ | alanine | benzyl | phenylalanine | formula (II) |
| ergovaline | H | $CH_3$ | alanine | $CH(CH_3)_2$ | valine | formula (I) |
| dihydroergovaline | H | $CH_3$ | alanine | $CH(CH_3)_2$ | valine | formula (II) |
| α-ergosine | H | $CH_3$ | alanine | $CH_2CH(CH_3)_2$ | leucine | formula (I) |
| dihydro-α-ergosine | H | $CH_3$ | alanine | $CH_2CH(CH_3)_2$ | leucine | formula (II) |
| β-ergosine | H | $CH_3$ | alanine | $CH(CH_3)CH_2CH_3$ (S) | isoleucine | formula (I) |
| dihydro-β-ergosine | H | $CH_3$ | alanine | $CH(CH_3)CH_2CH_3$ (S) | isoleucine | formula (II) |

As the compound of the present invention, a commercially available product may be used, or each compound can be produced by each method known per se. For example, a commercial source of each compound in the US can be known from Drugs@FDA (http://www.accessdata.fda.gov/scripts/cder/drugsatfda/index.cfm) and the like. Bromocriptine can be produced according to the methods described in, for example, U.S. Pat. Nos. 3,752,814, 3,752,888 and the like or a method analogous thereto, and other compounds can be produced similarly.

The compound of the present invention encompasses not only a free form but also a pharmacologically acceptable salt thereof. While the pharmacologically acceptable salt varies depending on the kind of the compound, examples thereof include base addition salts such as salts with inorganic base such as alkali metal salts (sodium salt, potassium salt etc.), alkaline earth metal salts (calcium salt, magnesium salt etc.), aluminum salt, ammonium salt and the like, and salts with organic base such as trimethylamine, triethylamine, pyridine, picoline, ethanolamine, diethanolamine, triethanolamine, dicyclohexylamine, N,N'-dibenzylethylenediamine and the like and the like, and acid addition salts such as salts with inorganic acid salt such as mesylate, hydrochloride, hydrobromide, sulfate, hydroiodide, nitrate, phosphate and the like, and salts with organic acid such as citrate, oxalate, acetate, formate, propionate, benzoate, trifluoroacetate, maleate, tartrate, methanesulfonate, benzenesulfonate, paratoluenesulfonate and the like, and the like.

When the compound of the present invention contains isomers such as an optical isomer, a stereoisomer, a regioisomer or a rotamer, any one of the isomers and mixtures are also encompassed in the compound. For example, when any one of compound described in Table 1 contains an optical isomer, an optical isomer resolved from racemate is also encompassed in the compound. These isomers can be obtained as single products by a synthesis method, a separation method (e.g., concentration, solvent extraction, column chromatography, recrystallization etc.), an optical resolution method (e.g., fractional recrystallization, chiral column method, diastereomer method etc.) and the like each known per se.

The compound of the present invention may be a crystal, and is included in the compound of the present invention whether it is in a single crystal form or a mixture of crystal forms. The crystal can be produced by crystallizing by applying a crystallization method known per se.

The compound of the present invention may be a solvate (e.g., hydrate etc.) or a non-solvate (e.g., non-hydrate etc.), both of which are encompassed in the compound of the present invention.

In addition, a compound labeled with an isotope (e.g., $^3$H, $^{14}$C, $^{35}$S, $^{125}$I etc.) etc. is also encompassed in the compound of the present invention.

In the present invention, Alzheimer's disease (AD) to be treated includes both sporadic and familial AD. In the case of familial AD, the causative gene is not particularly limited, and may be any known causative gene such as genes of Amyloid Precursor Protein (APP), Presenilin 1 (PSEN1), Presenilin 2 (PSEN2) and the like.

Examples of such APP mutation include dup APP mutation, APP KM670/671NL mutation, APP D678N mutation, APP E682K mutation, APP A692G mutation, APP E693K mutation, APP E693Q mutation, APP E693G mutation, APP E693del(APP E693Δ) mutation, APP D694N mutation, APP L705V mutation, APP A713T mutation, APP T714A mutation, APP T714I mutation, APP V715M mutation, APP V715A mutation, APP I716V mutation, APP I716F mutation, APP I716T mutation, APP V717I mutation and the like.

Examples of the presenilin 1 mutation include PSEN1 A79V mutation, PSEN1 V82L mutation, PSEN1 Δ183/M84 mutation, PSEN1 L85P mutation, PSEN1 V89L mutation, PSEN1 C92S mutation, PSEN1 V94F mutation, PSEN1 V96F mutation, PSEN1 V97L mutation, PSEN1 F105I mutation, PSEN1 F105L mutation, PSEN1 L113Q mutation, PSEN1 L113P mutation, PSEN1 Intron4; InsTAC mutation, PSEN1 Y115H mutation, PSEN1 Y115D mutation, PSEN1 Y115C mutation, PSEN1 T116N mutation, PSEN1 T116I mutation, PSEN1 P117A mutation, PSEN1 P117S mutation, PSEN1 P117R mutation, PSEN1 P117L mutation, PSEN1 E120K mutation, PSEN1 E120D mutation, PSEN1 E123K mutation, PSEN1 N135D mutation, PSEN1 N135S mutation, PSEN1 A136G mutation, PSEN1 F139V mutation, PSEN1 F139K mutation, PSEN1 F139T mutation, PSEN1 F139I mutation, PSEN1 I143F mutation, PSEN1 I143N mutation, PSEN1 I143T mutation, PSEN1 F146L mutation, PSEN1 F146V mutation, PSEN1 F146I mutation, PSEN1 T147I mutation, PSEN1 L153V mutation, PSEN1 Y154N mutation, PSEN1 Y154C mutation, PSEN1 InsFI mutation, PSEN1 H163Y mutation, PSEN1 H163R mutation, PSEN1 W165G mutation, PSEN1 W165C mutation, PSEN1 L166del mutation, PSEN1 L166H mutation, PSEN1 L166P mutation, PSEN1 L166R mutation, PSEN1 G1I67 mutation, PSEN1 ΔI168 mutation, PSEN1 S169P mutation, PSEN1 S169L mutation, PSEN1 S170F mutation, PSEN1 L171P mutation, PSEN1 L173W mutation, PSEN1 L173F mutation, PSEN1 L174F mutation, PSEN1 L174R mutation, PSEN1 F177L mutation, PSEN1 F177S mutation, PSEN1 S178P mutation, PSEN1 G183V mutation, PSEN1 E184D mutation, PSEN1 G206S mutation, PSEN1 G206D mutation, PSEN1 G206A mutation, PSEN1 G206V mutation, PSEN1 G209R mutation, PSEN1 G209E mutation, PSEN1 G209V mutation, PSEN1 I213L mutation, PSEN1 I213F mutation, PSEN1 I213T mutation, PSEN1 H214D mutation, PSEN1 H214Y mutation, PSEN1 G217D mutation, PSEN1 L219F mutation, PSEN1 L219P mutation, PSEN1 Q222R mutation, PSEN1 Q222H mutation, PSEN1 Q223R mutation, PSEN1 L226F mutation, PSEN1 L226R mutation, PSEN1 I229F mutation, PSEN1 A231T mutation, PSEN1 A231V mutation, PSEN1 F233L mutation, PSEN1 F233V mutation, PSEN1 F233T mutation, PSEN1 F233I mutation, PSEN1 L235V mutation, PSEN1 L235P mutation, PSEN1 F237I mutation, PSEN1 F237L mutation, PSEN1 T245P mutation, PSEN1 A246E mutation, PSEN1 L248R mutation, PSEN1 L250V mutation, PSEN1 L250S mutation, PSEN1 Y256S mutation, PSEN1 A260V mutation, PSEN1 V261L mutation, PSEN1 V261F mutation, PSEN1 L262F mutation, PSEN1 C263R mutation, PSEN1 C263F mutation, PSEN1 P264L mutation, PSEN1 G266S mutation, PSEN1 P267S mutation, PSEN1 P267L mutation, PSEN1 R269G mutation, PSEN1 R269H mutation, PSEN1 L271V mutation, PSEN1 V272A mutation, PSEN1 E273A mutation, PSEN1 T274R mutation, PSEN1 R278K mutation, PSEN1 R278T mutation, PSEN1 R278I mutation, PSEN1 R278S mutation, PSEN1 E280A mutation, PSEN1 E280G mutation, PSEN1 L282V mutation, PSEN1 L282F mutation, PSEN1 L282R mutation, PSEN1 P284S mutation, PSEN1 P284L mutation, PSEN1 A285V mutation, PSEN1 L286V mutation, PSEN1 L236P mutation, PSEN1 A9 mutation, PSEN1 Δ9Finn mutation, PSEN1 869-22_869-23ins18 mutation, PSEN1 T291P mutation, PSEN1 R358Q mutation, PSEN1 S365A mutation, PSEN1 S365Y mutation, PSEN1 R377F mutation, PSEN1 G378E mutation, PSEN1 G378V mutation, PSEN1 L381V mutation, PSEN1 G384A mutation, PSEN1 F386S mutation, PSEN1 S390I mutation, PSEN1 V391F mutation, PSEN1 L392V mutation, PSEN1 L392P mutation, PSEN1 G394V mutation, PSEN1 N405S mutation, PSEN1 A409T mutation, PSEN1 C410Y mutation, PSEN1 V412I mutation, PSEN1 L418F mutation, PSEN1 L420R mutation, PSEN1 L424V mutation, PSEN1 L424F mutation, PSEN1 L424H mutation, PSEN1 L424R mutation, PSEN1 A426P mutation, PSEN1 A431E mutation, PSEN1 A431V mutation, PSEN1 A434C mutation, PSEN1 L435F mutation, PSEN1 P436S mutation, PSEN1 P436Q mutation, PSEN1 I439V mutation, PSEN1 ΔT440 mutation and the like.

Examples of the presenilin 2 mutation include PSEN2 R71W mutation, PSEN2 A85V mutation, PSEN2 T122P mutation, PSEN2 T122R mutation, PSEN2 N141I mutation, PSEN2 V148I mutation, PSEN2 F174V mutation, PSEN2 S175C mutation, PSEN2 Y231C mutation, PSEN2 Q228L mutation, PSEN2 F239V mutation, PSEN2 F239I mutation, PSEN2 T430F mutation, PSEN2 D439A mutation and the like.

In the medicament of the present invention, when two or more compounds of the present invention are used or used in combination with other therapeutic drug, these compounds may be each formulated singly or produced as a combination agent. In the former case, each preparation can be administered to the same subject simultaneously or with time lag.

The medicament of the present invention can be administered orally or parenterally in the form of the compound of the present invention as it is alone as the active ingredient, or as a pharmaceutical composition in an appropriate dosage form blended with a pharmacologically acceptable carrier, excipient, diluent and the like.

As the composition for oral administration, solid or liquid dosage forms, specifically tablets (including sugar-coated tablets and film-coated tablets), pills, granules, powders, capsules (including soft capsules), syrups, emulsions, suspensions and the like can be mentioned. Meanwhile, as examples of the composition for parenteral administration, injections, suppositories and the like are used; the injections may include dosage forms such as intravenous injections, subcutaneous injections, intracutaneous injections, intramuscular injections and drip transfusion injections. These preparations are produced by a well-known method using additives, including excipients (e.g., organic excipients like sugar derivatives such as lactose, sucrose, glucose, mannitol, and sorbitol; starch derivatives such as cornstarch, potato starch, α starch, and dextrin; cellulose derivatives such as crystalline cellulose; gum arabic; dextran; and an organic excipient such as pullulan; and inorganic excipients like silicate derivatives such as light anhydrous silicic acid, synthetic aluminum silicate, calcium silicate, and magnesium metasilicoaluminate; phosphates such as calcium hydrogen phosphate; carbonates such as calcium carbonate; and sulfates such as calcium sulfate), lubricants (e.g., stearic acid, metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL leucine; lauryl sulfates such as sodium lauryl sulfate and magnesium lauryl sulfate; silicates such as silicic anhydride and silicic hydrates; and the aforementioned starch derivatives), binders (e.g., hydroxypropylcellulose, hydroxypropylmethylcellulose, polyvinylpyrrolidone, macrogol, and the same compounds as the aforementioned excipients), disintegrants (e.g., cellulose derivatives such as low-substitutional hydroxypropylcellulose, carboxymethylcellulose, carboxymethylcellulose calcium, and internally crosslinked carboxymethylcellulose sodium; chemically modified starches and celluloses such as carboxymethylstarch, carboxymethylstarch sodium, and crosslinked polyvinylpyrrolidone), emulsifiers (e.g., colloidal clays such as bentonite and Veegum; metal hydroxides such as magnesium hydroxide and aluminum hydroxide; anionic surfactants such as sodium lauryl sulfate and calcium stearate; cationic surfactants such as benzalkonium chloride; and non-ionic surfactants such as polyoxyethylene alkyl ethers, polyoxyethylene sorbitan fatty acid ester, and sucrose fatty acid ester), stabilizers (para-oxybenzoic acid esters such as methyl paraben and propyl paraben; alcohols such as chlorobutanol, benzyl alcohol, and phenylethyl alcohol; benzalkonium chloride; phenols such as phenol and cresol; thimerosal; dehydroacetic acid; and sorbic acid), taste/odor correctives (e.g., sweeteners, souring agents, and flavors in common use), diluents and the like.

The dose of the compound of the present invention as the active ingredient of the medicament of the present invention may be variable according to various conditions such as the kind of compound, the symptoms, age, weight, drug receptivity of a subject and the like. At least 0.1 mg (suitably 0.5 mg) to at most 1000 mg (suitably 500 mg) per dose for oral administration, or at least 0.01 mg (suitably 0.05 mg) to at most 100 mg (suitably 50 mg) per dose for parenteral administration, can be administered to an adult 1 to 6 times a day. The dose may be increased or reduced according to the symptoms. In particular, when the compound of the present invention is already on the market as a pharmaceutical product for diseases other than the above-mentioned diseases, an appropriate dose for each compound can be determined within the range confirmed to be safe. For example, the information relating to the safety of compounds is available from DailyMed (http://dailymed.nlm.nih.gov/dailymed/index.cfm) run by the United States National Library of Medicine.

Furthermore, the medicament of the present invention may be used in combination with other drugs, for example, compounds having known Aβ pathology improving effect such as BACE inhibitor IV, JNJ-40418677, Semagacestat, Acitretin and the like, existing therapeutic drugs for AD such as Sulfide slindac, Imanitib, Flurbiprofen, Donepezil, Rivastigmine, Galanthamine, Memantin and the like, and compounds having an Aβ production-lowering action, which were found by the present inventors, such as Cilostazol, Cromolyn, Fluvastatin, Probucol, Topiramate and the like. When used in combination, a preferred combination is, for example, a combination of the compound of the present invention, Cromolyn and Topiramate, or a combination of the compound of the present invention, Cilostazol and Probucol. The medicament of the present invention and these other drugs can be administered simultaneously, sequentially, or separately.

A prophylactic and/or treatment method including administration of an effective amount of the compound of the present invention or the medicament of the present invention to a mammal (animal to be the subject of the prophylaxis and/or treatment) is also included in the present invention. As the animal, mouse, rat, hamster, rabbit, cat, dog, bovine, sheep, monkey, human) can be mentioned, and preferred is human. The effective amount, dose and other items are as described in the above.

The present invention is explained in more detail in the following by referring to Examples, which are not to be construed as limitative.

EXAMPLE

In the below-mentioned Example, the experiment was performed as shown below.

1. Production of Nerve Cell

Differentiation into cerebral cortex nerve cells was induced from iPS cells established from a familial Alzheimer's disease patient with a G384A heterozygous mutation in the presenilin 1 gene and used for an assay. To induce differentiation into cerebral cortex nerve cell, human iPS cells were differentiated into cerebral cortical nerve by introducing Neurogenin2 gene into the iPS cells and allowing same to transiently express for 5 days by adding doxycycline.

2. Adjustment of Compound

The compounds of Table 2 were all dissolved in DMSO at 25 mM and used.

TABLE 2

| compound name | catalog No. | classification |
|---|---|---|
| Dopamine HCl | 1421271 nacalai 1 g | pan dopamine agonist |
| SKF38393 hydrochloride | ab120740 ABCAM 100 mg | D1/5 agonist |
| PD 168077 | ab120568 ABCAM 10 mg | D4 agonist |
| B-HT 920 dihydrochloride | Sigma B162 25 mg | D2 agonist without ergot structure |
| Pramipexole dihydrochloride | Sigma A1237-10 mg | D2 agonist without ergot structure |
| Ropinirole hydrochloride | Abcam AB120575-10 10 mg | D2 agonist without ergot structure |
| Bromocriptine mesylate | 020-18471 wako 25 mg | D2 agonist with ergot structure |
| Cabergoline | Abcam AB120564-10 10 mg | D2 agonist with ergot structure |
| Pergolide mesylate | MP Biomed 194176 | D2 agonist with ergot structure |
| Ergocristine | FERMENTAS EC001 | bromocriptine analog compound |
| Diergotamine | TOCRIS 0475/100 | bromocriptine analog compound |
| Alpha-Ergocryptine | TORONTO E597500 | bromocriptine analog compound |
| ERGOTAMINE TARTRATE | TCI Tokyo Chemical Industry Co., Ltd. E0019 100 mg | bromocriptine analog compound |
| Dihydroergocristine mesylate | sc-201117 200 mg Santacruz | bromocriptine analog compound |

3. Aβ Assay

Cerebral cortex nerve cells were seeded in a 96 well plate (Edge plate, CORNING) at 100,000/well. After 3 days, the total amount of the medium was changed, during which various concentrations of compounds were added. After 48 hr, the medium was recovered, contamination with dead cell was prevented by a centrifugation treatment at 400 g for 5 min and the cells were preserved at −80° C. until Aβ measurement.

For the measurement of trace Aβ in the culture supernatant, SECTOR Imager 2400 (Meso Scale Discovery, U.S.A) was used as a detection apparatus, and SULFO-TAG-labeled antibody was detected by the electric chemiluminescent method and quantified. The culture supernatant (25 µL) frozen at −80° C. was thawed on ice, and the concentrations of Aβ1-40, 1-42 in the culture supernatant were respectively measured according to the kit protocol of the Human (6E10) Abeta 3-Plex Base Kit (Meso Scale Discovery, U.S.A).

Example 1: Search for Medicaments that Decrease Aβ Production

Figure 1:
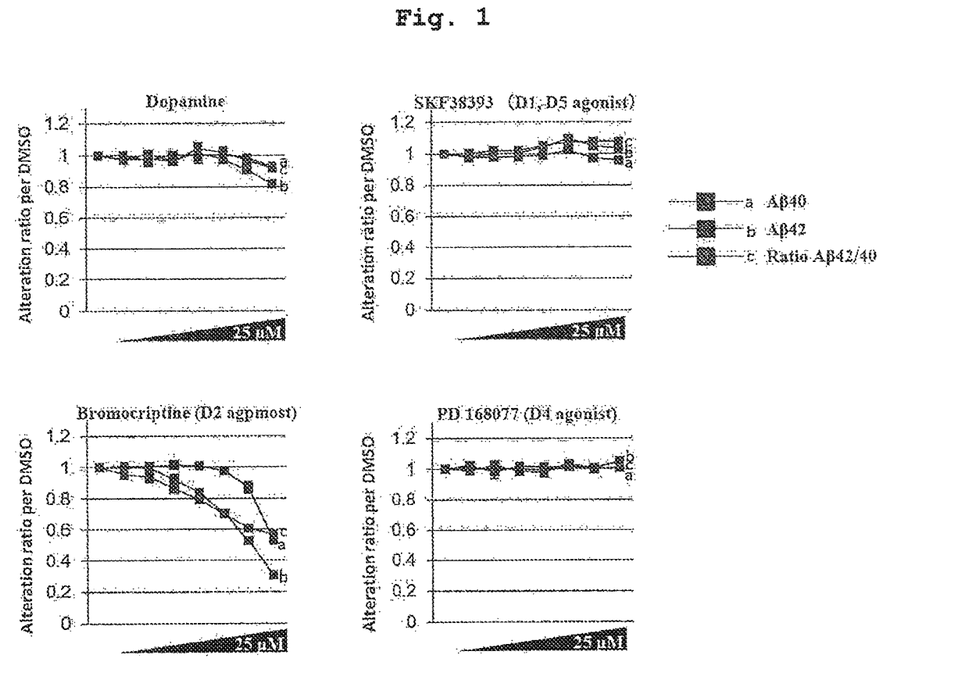
FIG. 1 shows the results of the Aβ production-lowering action by dopamine receptor stimulation using dopamine hydrochloride, SKF38393, bromocriptine or PD168077. The horizontal axis shows the concentration of the added compound in the medium, and the vertical axis shows the relative proportion of Aβ production amount when compared with the control added with DMSO (each n=3). The error bar shows standard deviation.

Differentiation into cerebral cortex nerve cell from pluripotent stem cell (iPS cell) established from familial Alzheimer's disease (Alzheimer's disease: AD) patients was induced by a rapid method with high purity and high reproducibility. Using this nerve cell, an experimental system to monitor the metabolic dynamics of amyloid β protein (amyloid beta: Aβ), which is a pathogenic substance of AD was constructed. Since this AD patient-derived cerebral cortex nerve cell has a G384A heterozygote mutation in PSEN1, the causative gene of familial AD, the production of the Aβ42 subtype known as toxic Aβ increases, and the ratio Aβ42/40 to the production of the most abundant Aβ40 subtype is high. Using this experimental system, screening analysis of existing drug libraries was conducted and a medicament that decreases Aβ production was searched for. As a result of the search, it was found that addition of bromocriptine (bromocriptine mesylate) decreases the production of Aβ (FIG. 1). The Aβ production-lowering action more efficiently reduced the production of Aβ42 subtype than Aβ40, resulting in lower Aβ42/40 ratio (FIG. 1).

Example 2: Study of Relationship Between Lower Aβ Production and Dopamine Receptor Stimulation Action Bromocriptine has been approved as a therapeutic drug for Parkinson's disease because it has an agonistic action on dopamine receptors (dopaminergic receptor (DR)). To determine whether the dopamine receptor stimulation action decreases Aβ production or whether the structure itself of bromocriptine decreases Aβ production by a mechanism that is not mediated by a dopamine receptor, the following was studied.

(1) Study of Aβ Production-Lowering Action and DR (Dopamine Receptor) Subtype

Bromocriptine has a high affinity for, among DRs, type 2 DR (dopamine receptor type 2: D2R) and has high D2R selectivity. Therefore, whether stimulation of DR subtypes other than D2R changes Aβ production was studied. SKF38393 which is a DR agonist selective for type 1 and type 5, PD168077 which is a DR agonist selective for type 4 DR, and further, dopamine hydrochloride which is a non-selective DR agonist were respectively added at 0.0016, 0.008, 0.04, 0.2, 1, 5, 25 µM to cerebral cortex nerve cells. However, none of the compounds changed Aβ production (FIG. 1). These results specified that type 1 DR, type 4 and type 5 DR stimuli were not involved in Aβ production.

Figure 2:
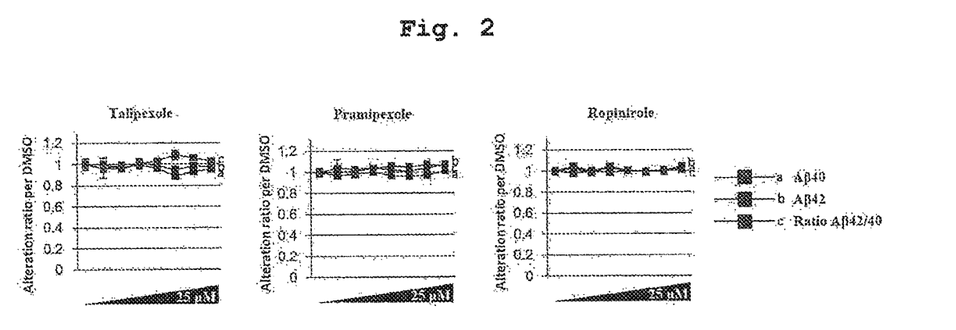
FIG. 2 shows the results of the A3 production-lowering action by non-ergot dopamine receptor type 2 agonists (Talipexole, Pramipexole, Ropinirole). The horizontal axis shows the concentration of the added compound in the medium, and the vertical axis shows the relative proportion of Aβ production amount when compared with the control added with DMSO (each n=3). The error bar shows standard deviation.

(2) Study of Aβ Production-Lowering Action and Type 2 DR Receptor Stimulation Action Next, whether the Aβ production-lowering action of bromocriptine was due to D2R agonistic action or other than D2R stimulation pathway was investigated. Bromocriptine is classified as an ergot D2R agonist because of the characteristics of its skeleton structure. On the other hand, non-ergot D2R agonists that do not have an ergot structure are also widely applied clinically as therapeutic drug for Parkinson's disease; however, the compound structure is significantly different from that of bromocriptine. As the non-ergot D2R agonist, Talipexole (B-HT 920 dihydrochloride), Pramipexole dihydrochloride, Ropinirole hydrochloride were respectively added to cerebral cortex nerve cell at concentrations of 0.0016, 0.008, 0.04, 0.2, 1, 5, 25 µM. However, none of the compounds changed Aβ production (FIG. 2).

Figure 3:
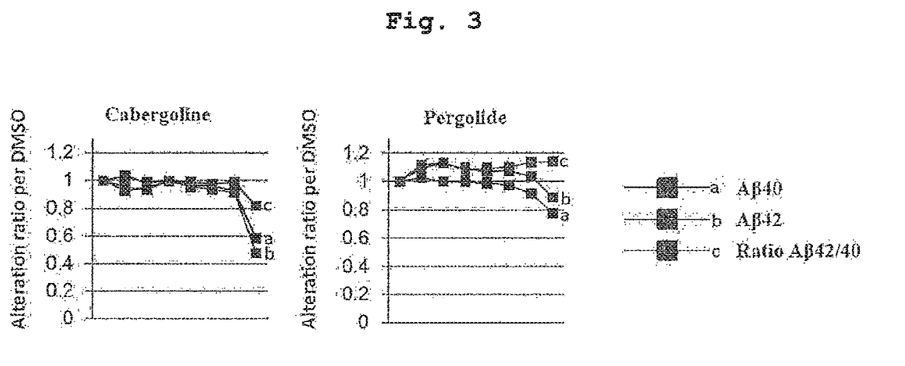
FIG. 3 shows the results of the Aβ production-lowering action by ergot dopamine receptor type 2 agonists (Cabergoline, Pergolide). The horizontal axis shows the concentration of the added compound in the medium, and the vertical axis shows the relative proportion of Aβ production amount when compared with the control added with DMSO (each n=3).

On the other hand, Cabergoline, Pergolide mesylate were added as ergot D2R agonists to cerebral cortex nerve cell at concentrations of at 0.0016, 0.008, 0.04, 0.2, 1, 5, 25 µM. As a result, Cabergoline showed an Aβ production-lowering action at 25 µM and Pergolide mesylate showed an Aβ production-lowering action at 5, 25 µM (FIG. 3).

These results suggest that the structure itself of bromocriptine is important for the Aβ production-lowering action of bromocriptine, not the D2R receptor stimulating action.

(3) Search for Relationship Between Compound with Ergoline Skeleton and Aβ Production-Lowering Action Bromocriptine, which is an ergot D2R agonist, has a peptide-type alkaloid structure in which three peptides of proline, valine and leucine are bonded to an ergoline ring structure. The peptide-type alkaloid structure is known to include various analogous compounds having different physiological activities depending on the combination of the three peptides bonded to the ergoline ring skeleton. Whether the Aβ production-lowering action of bromocriptine is commonly seen in these structures, and which of the analogous structures is useful for the Aβ production-lowering action were studied.

To search for bromocriptine analog compounds, bromocriptine structure described in the SMILES format was read in the ChEMBL database (https://www.ebi.ac.uk/chembl/) and a similarity search was performed (http://www.ebi.ac.uk/chebi/userManualForward.do). As a result, a based on the Tanimoto coefficient, compounds with high similarity were searched for out of 1,928,903 compounds registered in the DB:ChEMBL_version 21, the cutoff was set to not less than 80%, commercially available alpha-ergocryptine, ergocristine, ergotamine tartrate, dihydroergocristine mesylate, dihydroergotamine mesylate were extracted and the Aβ production-lowering action was studied (Table 3)

TABLE 3

| | Similarity % to "bromocriptine mesylate" | Clinical Phase | Molecular weight | ALogP | PSA | Num Ro5 Violations | Mechanism of Action |
|---|---|---|---|---|---|---|---|
| Bromocriptine Mesylate | 100 | 4 Parkinson disease | 654.59 | 4.36 | 118.21 | 1 | D2-like dopamine receptor agonist |
| Alpha-Ergocryptine | 92.49 | 0 | 575.7 | 3.8 | 118.2 | 1 | N.A. |
| Ergocristine | 90.74 | 0 | 609.71 | 4.12 | 118.21 | 1 | N.A. |
| Ergotamine Tartrate | 89.1 | 4 Migraine | 581.66 | 3.02 | 118.2 | 1 | Adrenergic receptor alpha agonist Serotonin 1d (5-HT1d) receptor agonist |
| Dihydroergocristine mesylate (GNF-Pf-3462) | 89.81 | 0 | 611.73 | 4.3 | 118.21 | 1 | N.A. |
| Dihydroergotamine Mesylate | 88.2 | 4 Migraine | 583.68 | 3.2 | 118.21 | 1 | Serotonin 1d (5-HT1d) receptor agonist |

Bromocriptine analog
ALogP: Calculated value for the lipophilicity of a molecule expressed as log ALogP < 3 polar surface area
(PSA): index of membrane permeability PSA ≥ 75 Å2
Num Ro5 Violations: Number of properties defined in Lipinski's Rule of 5 (R05) that the compound fails. (https://www.ebi.ac.uk/chemblntd/glossary)

The six compounds described in Table 3 have the following chemical structures:

Bromocriptine Mesylate

Alpha Ergocryptine

Ergocristine

Ergotamine Tartrate

Dihydroergocristine mesylate (GNF-PF-3462)

Dihydroergotamine Mesylate

Figure 4:
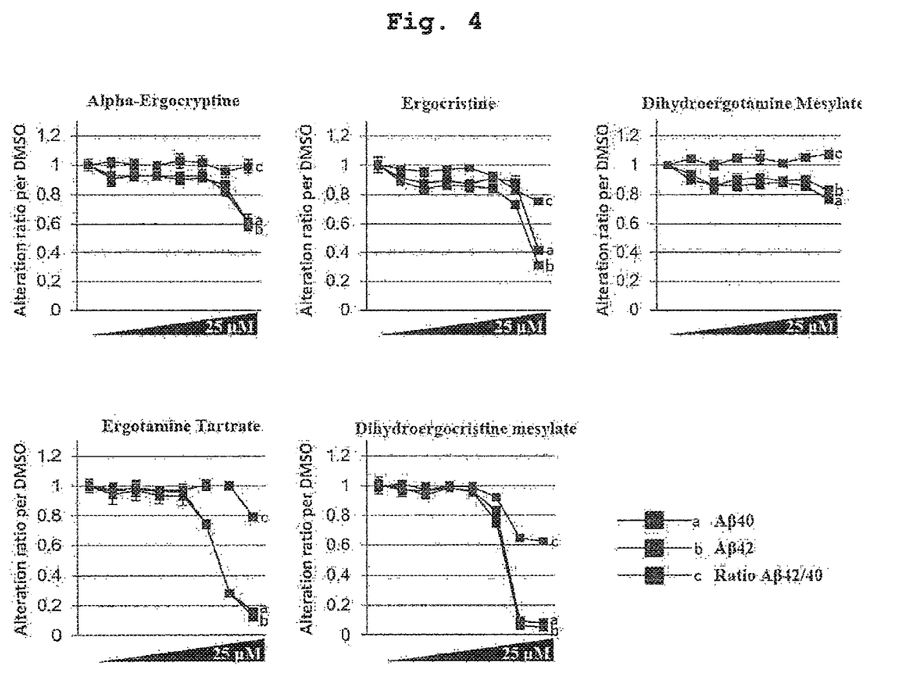
FIG. 4 shows the results of the Aβ production-lowering action by bromocriptine analog compounds (Alpha-Ergocryptine, Ergocristine, Dihydroergotamine Mesylate, Ergotamine Tartrate, Dihydroergocristine mesylate). The horizontal axis shows the concentration of the added compound in the medium, and the vertical axis shows the relative proportion of Aβ production amount when compared with the control added with DMSO (each n=3). The error bar shows standard deviation.

All these drugs showed an Aβ production-lowering action similar to that of bromocriptine (FIG. 4). Among them, α-ergocryptin having no bromo group in the ergoline ring structure of bromocriptine showed an Aβ production-lowering action similar to that of bromocriptine; however, it also lowered Aβ40 and 42 to the same degree, and the Aβ42/40 ratio did not change. This indicates that modification with the bromo group in the ergoline ring structure is important for decreasing the Aβ42/40 ratio.

Furthermore, the combination of the three peptides contained in the peptide-type alkaloid structure has no significant effect on the weight of the Aβ production-lowering action, and ergocristine (proline•valine phenylalanine), ergotamine tartrate (proline•alanine•phenylalanine), dihydroergocristine mesylate (proline•valine phenylalanine), dihydroergotamine mesylate (proline•alanine-phenylalanine) showed a similar Aβ production-lowering action.

From the above, it was shown that the structure of peptide-type ergot alkaloid acts to lower the Aβ production amount, and further that modification with the bromo group at position 2 in the ergoline ring structure is important for the Aβ42/40 ratio-lowering action.

This application is based on a patent application No. 2017-126808 filed in Japan (filing date: Jun. 28, 2017), the contents of which are incorporated in full herein.

INDUSTRIAL APPLICABILITY

The compound of the present invention is useful for the prophylaxis and/or treatment of Alzheimer's disease. Particularly, since clinical and nonclinical data of safety and is the like of medicaments already on the market as pharmaceutical products for other diseases have been accumulated, and the libraries of neighboring compounds already exist, a pharmaceutical product capable of preventing and/or treating neurodegenerative disease may be developed rapidly at a low cost.

The invention claimed is:

1. A method for treating Alzheimer's disease caused by mutation of presenilin 1 in a mammal in need thereof comprising administering an effective amount of bromocriptine or a salt thereof to the mammal, wherein the method comprises reducing the ratio of the production of amyloid beta peptide 1-42 (Aβ42) subtype to the production of amyloid beta peptide 1-40 (Aβ40) subtype (Aβ42/40 ratio) from cerebral cortex nerve cells in the subject.

2. A method for delaying the onset and/or slowing the progression of Alzheimer's disease caused by mutation of presenilin 1 in a mammal in need thereof comprising administering an effective amount of bromocriptine or a salt thereof to the mammal, wherein the method comprises reducing the ratio of the production of amyloid beta peptide 1-42 (Aβ42) subtype to the production of amyloid beta peptide 1-40 (Aβ40) subtype (Aβ42/40 ratio) from cerebral cortex nerve cells in the subject.

* * * * *